United States Patent [19]

Schuetz et al.

[11] Patent Number: 5,106,852
[45] Date of Patent: Apr. 21, 1992

[54] PEST CONTROL WITH PYRIMIDINES

[75] Inventors: Franz Schuetz, Ludwigshafen; Siegbert Brand, Weinheim; Jochen Wild, Deidesheim; Thomas Kuekenhoehner, Frankenthal; Peter Hofmeister, Neustadt; Christoph Kuenast, Otterstadt, all of Fed. Rep. of Germany

[73] Assignee: BASF Aktiengesellschaft, Ludwigshafen, Fed. Rep. of Germany

[21] Appl. No.: 692,867

[22] Filed: Apr. 29, 1991

Related U.S. Application Data

[62] Division of Ser. No. 551,471, Jul. 12, 1990, Pat. No. 5,047,408.

[30] Foreign Application Priority Data

Jul. 13, 1989 [DE] Fed. Rep. of Germany ....... 3923068

[51] Int. Cl.$^5$ .................... C07D 239/32; A01N 43/54
[52] U.S. Cl. ..................................... 514/269; 544/319
[58] Field of Search .......................... 514/269; 544/319

[56] References Cited

PUBLICATIONS

Cliff et al., Chemical Abstracts, vol. 111, entry 7426n (1989).
Schuetz et al., Chemical Abstracts, vol. 113, entry 40460h (1990).

*Primary Examiner*—John M. Ford
*Attorney, Agent, or Firm*—Keil & Weinkauf

[57] ABSTRACT

Methods of combating pests with substituted pyrimidines of the formula I

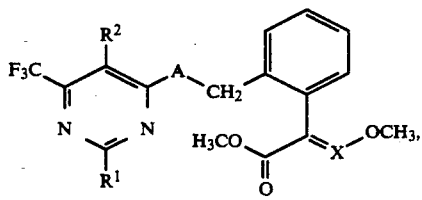

where $R^1$ is alkyl, cycloalkyl, haloalkyl, alkoxy, alkylthio or substituted or unsubstituted aryl, $R^2$ is halogen or hydrogen, A is oxygen or sulfur, and X is CH or N, and pyrimidines of the general formula Ia

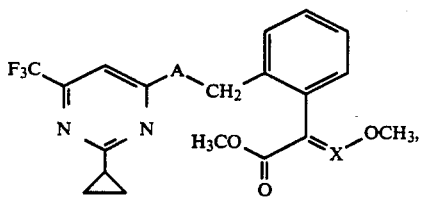

where A is oxygen or sulfur and X is CH or N, and pesticides containing these compounds.

2 Claims, No Drawings

PEST CONTROL WITH PYRIMIDINES

This is a divisional application of Ser. No. 07/551,471, filed July 12, 1990, now U.S. Pat. No. 5,047,408.

The present invention relates to a method for controlling insects and spider mites, which comprises allowing an amount, which is effective against the pests, of a substituted pyrimidine of the general formula I

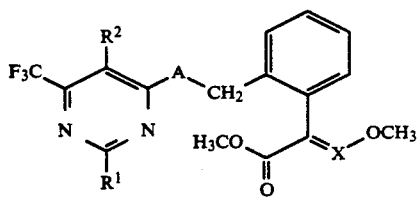

where
- $R^1$ is $C_1-C_6$-alkyl, $C_3-C_6$-cycloalkyl, $C_1-C_4$-haloalkyl, $C_1-C_4$-alkoxy, $C_1-C_4$-alkylthio, or aryl which is unsubstituted or monosubstituted or polysubstituted by $C_1-C_6$-alkyl, $C_1-C_4$-alkoxy or halogen,
- $R^2$ is halogen or hydrogen,
- A is oxygen or sulfur and
- X is CH or N, or of its plant-tolerated acid addition salt or metal complex to act on the pests or their habitat.

The present invention furthermore relates to pyrimidines of the general formula Ia

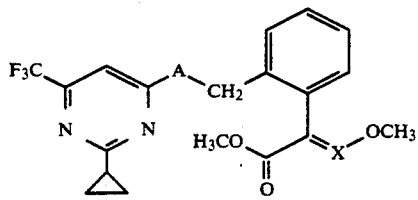

where A is oxygen or sulfur and X is CH or N, and pesticides which contain the pyrimidines Ia.

DE-A 38 23 991 and DE-A 38 35 028 describe substituted pyrimidines having fungicidal activity.

EP-A-256 667 discloses that methyl α-arylacrylates having heterocyclic substituents, for example methyl α-[2-(benzoxazol-2'-yloxy)-phenyl]-β-methoxyacrylate, can be used as insecticides. However, its insecticidal action is unsatisfactory.

Furthermore, EP-A-299 694 describes, inter alia, insecticidal compounds whose general formula covers the compounds of the formula I or Ia.

It is an object of the present invention to provide an effective method of controlling pests.

We have found that this object is achieved and that the pyrimidines I defined at the outset and their plant-tolerated acid addition salts or metal complexes have an excellent insecticidal and in particular acaricidal action, which is better than that of the known methyl α-arylacrylates.

We have furthermore found the pyrimidines of the formula Ia and pesticides containing them.

The radicals $R_1$ and $R_2$ in the general formula I may have, for example, the following meanings:
$R^1$ is $C_1-C_6$-alkyl (e.g. methyl, ethyl, n-propyl, isopropyl, n-butyl, isobutyl, sec-butyl, tert-butyl, n-pentyl, isopentyl, sec-pentyl, tert-pentyl, neopentyl or hexyl), $C_3-C_6$-cycloalkyl (e.g. cyclopropyl, cyclobutyl, cyclopentyl or cyclohexyl), $C_1-C_4$-haloalkyl (e.g. trifluoromethyl, 2,2,2-trifluoroethyl, pentafluoroethyl, chloromethyl, dichloromethyl or trichloromethyl), $C_1-C_4$-alkoxy (e.g. methoxy, ethoxy, n-propoxy, isopropoxy, n-butoxy, isobutoxy, sec-butoxy or tert-butoxy), $C_1-C_4$-alkylthio (e.g. methylthio, ethylthio, n-propylthio, isopropylthio or butylthio) or aryl (e.g. phenyl), where the aromatic ring may be unsubstituted or substituted by one or more, in particular from one to three, of the following radicals: $C_1-C_6$-alkyl (e.g. methyl, ethyl, n-propyl, isopropyl, n-butyl, isobutyl, sec-butyl, tert-butyl, n-pentyl, isopentyl, sec-pentyl, tert-pentyl or neopentyl), $C_1-C_4$-alkoxy (e.g. methoxy, ethoxy, n-propoxy, isopropoxy, n-butoxy, isobutoxy, sec-butoxy or tert-butoxy) or halogen (e.g. fluorine, chlorine or bromine);

$R^2$ is halogen (e.g. fluorine, chlorine or bromine) or hydrogen.

Pyrimidines of the general formula I in which $R^1$ is n-propyl or cyclopropyl, $R^2$ is hydrogen, A is oxygen or sulfur, and X is CH or N are particularly suitable for controlling insects and spider mites.

Salts are, for example, the plant-tolerated acid addition salts, for example the salts with inorganic or organic acids, such as the salts of hydrochloric acid, hydrobromic acid, nitric acid, oxalic acid, acetic acid, sulfuric acid, phosphoric acid or dodecylbenzenesulfonic acid. The activity of the salts is due to the cation, so that any anion may in general be chosen.

Furthermore, the compounds of the formula I can be converted into metal complexes by known methods. This can be effected by reacting these compounds with metal salts, for example salts of the metals copper, zinc, iron, manganese or nickel, e.g. copper(II) chloride, zinc(II) chloride, iron(III) chloride, copper(II) nitrate, manganese (II) chloride or nickel(II) bromide.

The preparation of the compounds of the general formula I and accordingly of the compounds Ia is carried out, for example, by reacting a substituted pyrimidine of the general formula II or IIa with a substituted benzyl halide of the general formula III (where X has the abovementioned meanings and Y is Cl or Br).

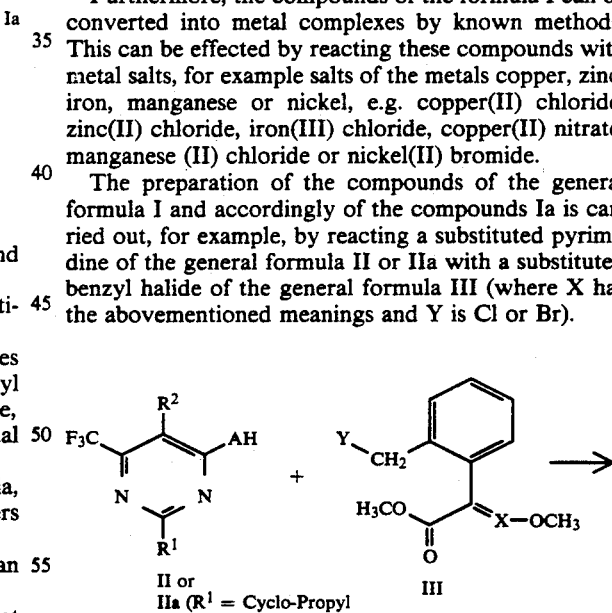

II or
IIa ($R^1$ = Cyclo-Propyl)

III

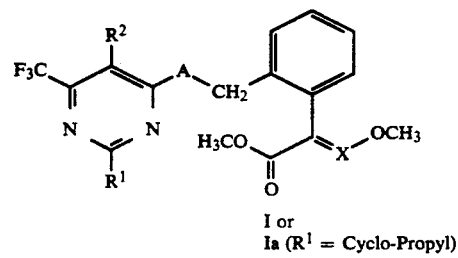

I or
Ia ($R^1$ = Cyclo-Propyl)

R[1], R[2] and X have the abovementioned meanings and Y is a conventional leaving group, e.g. chloride or bromide.

The reactions to obtain the compounds of the general formula I can be carried out, for example, in an inert solvent or diluent (e.g. acetone, acetonitrile, dimethyl sulfoxide, dioxane, dimethylformamide, N-methylpyrrolidone, N,N'-dimethylpropyleneurea or pyridine) with the use of a base (e.g. sodium carbonate or potassium carbonate). It may furthermore be advantageous to add a catalyst e.g. tris-(3,6-dioxoheptyl)-amine, to the reaction mixture (J. Org. Chem. 50 (1985), 3717).

In an alternative procedure, the compounds of the general formula II can first be converted with a base (e.g. sodium hydroxide or potassium hydroxide) into the corresponding sodium salts or potassium salts and the latter can then be reacted with substituted benzyl halides of the general formula III in an inert solvent or diluent (e.g. dimethylformamide) to give the corresponding substituted pyrimidines of the general formula I.

The pyrimidines of the general formula II which are required as starting compounds are either known or can be prepared by processes similar to known processes. Appropriate preparation processes are described in, for example, EP-A 224 217 or J. Heterocyclic Chem. 20 (1983), 219.

Methyl α-(2-halomethyl)-phenyl-β-methoxyacrylates of the general formula IIIa (X=CH, Y=Cl or Br) are either known or can be prepared by known processes. Appropriate preparation processes are described in, for example, DE-A-35 19 280, DE-A-35 45 318 and DE-A-35 45 319.

The 2-(halomethyl)-phenylglyoxylic acid methyl ester O-methyloximes of the general formula IIIb (X=N, Y=Cl or Br) are also required for the preparation of the substituted pyrimidines of the general formula I. They are obtained, for example, by halogenation of the 2-methylphenylglyoxylic acid methyl ester O-methyloxime IV by methods known from the literature, for example by free radical bromination or chlorination using bromine or chlorine in an inert solvent (e.g. tetrachloromethane), if necessary with exposure to a light source (e.g. Hg vapor lamp, 300 W) or by reaction with N-chloro- or N-bromosuccinimide (cf. Horner and Winkelmann, Angew. Chem. 71 1959), 349).

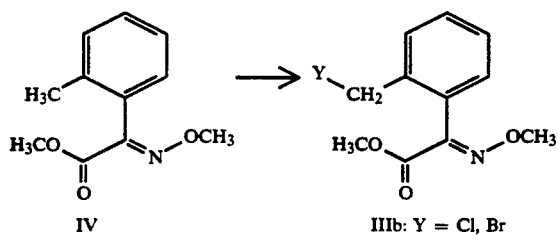

2-Methylphenylglyoxylic acid methyl ester O-methyloxime IV can be prepared by reacting methyl 2-methylphenylglyoxylate V

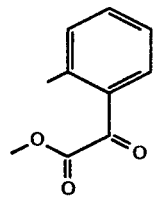

for example a) with O-methylhydroxylamine hydrochloride or b) with hydroxylamine hydrochloride to give the corresponding oxime and then reacting the latter with a methylating agent of the formula $CH_3$-L, where L is a leaving group (e.g. chloride, bromide, iodide or methylsulfate) (cf. DE-36 23 921).

The compounds of the general formula I may be obtained as E/Z isomer mixtures in the preparation, owing to the presence of the C=C or C=N double bond. These isomer mixtures can be separated into the individual components in a conventional manner, for example by crystallization or chromatography. Both the individual isomeric compounds and the mixtures thereof are subjects of the invention and can be used as insecticides.

EXAMPLES

The Examples and methods which follow illustrate the preparation of the active ingredients and their intermediates.

EXAMPLE 1

Methyl α-[2-(2'-n-propyl-6'-trifluoromethyl-4'-pyrimidinyl)-oxymethylphenyl]-β-methoxyacrylate (compound no. 9)

20.6 g (0.1 mol) of 2-n-propyl-6-trifluoromethyl-4-hydroxypyrimidine, 28.5 g (0.1 mol) of methyl α-(2-bromomethyl)-phenyl-β-methoxyacrylate and 20.7 g (0.15 mol) of potassium carbonate in 250 ml of dimethylformamide are stirred for 48 hours at room temperature. Thereafter, the reaction mixture is taken up in water and extracted with diethyl ether. The organic phase is washed with water, dried over magnesium sulfate and evaporated down. The resulting oil is filtered over silica gel (methylene chloride). After removal of the solvent, 16.2 g (40%) of the title compound are obtained in the form of colorless crystals of melting point 81°-82° C.

EXAMPLE 2

α-[2-(2'-Methyl-6'-trifluoromethyl-4'-pyrimidinyl)-thiomethylphenyl]-glyoxylic acid methyl ester O-methyloxime (compound no. 4)

Method 1: 2-(Bromomethyl)-phenylglyoxylic acid methyl ester O-methyloxime 21.4 g (0.133 mol) of bromine are added, while stirring, to 27.5 g (0.133 mol) of 2-methylphenylglyoxylic acid methyl ester O-methyloxime dissolved in 400 ml of tetrachloromethane. The mixture is then refluxed for four hours while being exposed to a 300 W Hg vapor lamp, after which it is evaporated down, the residue is taken up in ethyl acetate/water and the solution is washed with water, dried with sodium sulfate and evaporated down. The crude product is purified by chromatography over silica gel, using 9:1 cyclohexane/ethyl acetate. 17.4 g (46%) of the abovementioned compound are obtained as an oil.

Method 2

9.7 g (0.05 mol) of 2-methyl-6-trifluoromethyl-4-mercaptopyrimidine, 14.3 g (0.05 mol) of 2-(bromomethyl)-phenylglyoxylic acid methyl ester O-methyloxime and 11.0 g (0.08 mol) of potassium carbonate in 125 ml of dimethylformamide are stirred for 48 hours at room temperature. Thereafter, the reaction mixture is evaporated down, the residue is taken up in methylene chloride and the organic phase is washed with water and dried over magnesium sulfate. The oil obtained after evaporation is triturated with methyl tert-butyl ether/hexane. 6.3 g (32%) of the title compound are obtained in the form of colorless crystals of melting point 60°–61° C.

The following compounds can be prepared in a similar manner:

TABLE 1

Compounds of the general formula I.

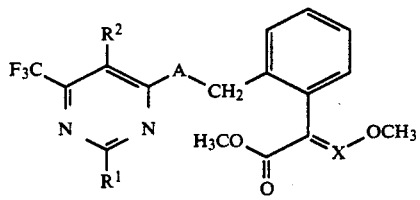

| No. | $R^1$ | $R^2$ | A | X | mp.: (°C.) |
|---|---|---|---|---|---|
| 1 | CH₃ | H | O | CH | 95–96 (E) |
| 2 | CH₃ | H | O | N | |
| 3 | CH₃ | H | S | CH | oil (E) |
| 4 | CH₃ | H | S | N | 60–61 (E) |
| 5 | C₂H₅ | H | O | CH | |
| 6 | C₂H₅ | H | O | N | |
| 7 | C₂H₅ | H | S | CH | |
| 8 | C₂H₅ | H | S | N | |
| 9 | n-C₃H₇ | H | O | CH | 81–82 (E) |
| 10 | n-C₃H₇ | H | O | N | 73–75 (E) |
| 11 | n-C₃H₇ | H | S | CH | |
| 12 | n-C₃H₇ | H | S | N | |
| 13 | cyclo-C₃H₅ | H | O | CH | 73–74 (E) |
| 14 | cyclo-C₃H₅ | H | O | N | 98–100 (E) |
| 15 | cyclo-C₃H₅ | H | S | CH | |
| 16 | cyclo-C₃H₅ | H | S | N | |
| 17 | t-C₄H₉ | H | O | CH | oil (E) |
| 18 | t-C₄H₉ | H | O | N | 96–98 (E) |
| 19 | t-C₄H₉ | H | S | CH | |
| 20 | t-C₄H₉ | H | S | N | |
| 21 | CF₃ | H | O | CH | 57–58 (E) |
| 22 | CF₃ | H | O | N | |
| 23 | CF₃ | H | S | CH | |
| 24 | CF₃ | H | S | N | |
| 25 | SCH₃ | H | O | CH | 110–112 (E) |
| 26 | SCH₃ | H | O | N | |
| 27 | SCH₃ | H | S | CH | |
| 28 | SCH₃ | H | S | N | |
| 29 | SCH₃ | Cl | O | CH | oil (E) |
| 30 | SCH₃ | Cl | O | N | |
| 31 | SCH₃ | Cl | S | CH | |
| 32 | SCH₃ | Cl | S | N | |
| 33 | C₆H₅ | H | O | CH | 109–110 (E) |
| 34 | C₆H₅ | H | O | N | |
| 35 | C₆H₅ | H | S | N | |
| 36 | C₆H₅ | H | S | N | |

The configuration statement refers to the methyl β-methoxyacrylate group or the glyoxylic acid methyl ester-O-methyloxime group.

The substituted pyrimidines of the formula I are suitable for effectively combating pests such as insects, arachnids and nematodes. They may be used as pesticides in crop protection and in the hygiene, stores protection and veterinary sector.

Examples of injurious insects belonging to the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chemiatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipapula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella*

*tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the Homoptera order are *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii.*

Examples from the Isoptera order are *Calotermes flavicollis, Leucotermes flavipes, Reticulitermes lucifugus* and *Termes natalensis.*

Examples from the Orthoptera order are *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

Examples from the Acarina order are *Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae.*

Examples from the nematode class are root-knot nematodes, e.g., *Meloidogyne hapla, Meloidogyne incognita* and *Meloidogyne javanica,* cyst-forming nematodes, e.g., *Globodera rostochiensis, Heterodera avenae, Hetrodera glycinae, Heterodera schachtii* and *Heterodera trifolii,* and stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, napthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or napthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Examples of formulations are given below.

I. 5 parts by weight or compound no. 3 is intimately mixed with 95 parts by weight of particulate kaolin. A dust is obtained containing 5% by weight of the active ingredient.

II. 30 parts by weight of compound no. 9 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 4 is dissolved in a mixture consisting of 90 parts by weight of xylene, 6 parts by weight of the adduct of 8 to 10 moles of ethylene oxide and 1 mole of oleic acid-N- monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 21 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 33 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may vary over a wide range. Generally, they are from 0.0001 to 10, and preferably from 0.01 to 1, %.

The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.02 to 10, particularly from 0.1 to 2.0, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

USE EXAMPLES

In the following examples, compound no. 9 was investigated as to its action on *Tetranychus telarius* and *Plutella maculipennis*, and compound no. 13 as to its action on *Tetranychus telarius*. The purity of the active ingredients was >95%. The active ingredient was used as a 10% emulsion concentrate obtained by emulsifying the active ingredient in a mixture consisting of 70 wt % of cyclohexanone, 20 wt % of Nekanil® LN (≅ Lutensol AP6, a spreadersticker with an emulsifying and dispersing action based on ethoxylated alkylphenols) and 10 wt % of Emulphor® EL (≅ Emulan® EL, an emulsifier based on ethoxylated fatty alcohols). The concentrations given in the examples were obtained by diluting the formulated active ingredient with water.

EXAMPLE 1

Action of ingested food on *Plutella maculipennis* (diamondback moth)

Leaves of young kohlrabi plants were dipped for 3 seconds into aqueous emulsions of the active ingredients and placed, after excess liquid had been briefly allowed to drip off, on a moist filter paper in a Petri dish. 10 caterpillars of the fourth stage were placed on each leaf. The kill rate was determined after 48 hours.

A high kill rate was achieved at a concentration of 200 ppm of compound no. 9.

EXAMPLE 2

*Tetranychus telarius*, continuous contact action

Bean plants (*Phaseolus multiflorus*) are sprayed in conventional manner in a spray cabinet with aqueous formulations of the active ingredients. After the leaves have dried, pieces 25 mm in diameter are stamped out and placed on a piece of cellulose whose edges hang down into water. Five female adults of *Tetranychus telarius* are placed on each leaf, and the action is assessed after 6 and 12 days.

In this experiment, a concentration of 2 ppm of compound no. 9 achieved a good kill rate.

EXAMPLE 3

*Tetranychus telarius*, contact action, spray experiment

Potted bush beans exhibiting the second pair of true leaves are sprayed to runoff in a spray cabinet with aqueous formulations (approx. 50 ml) of the active ingredients. The plants are under heavy mite attack and bear numerous eggs.

The action is assessed after 5 days by means of a binocular microscope, attention being paid to the fact that all stages are covered. During this period, the plants are kept under normal greenhouse conditions.

In this experiment, a concentration of 100 ppm of compound no. 9 achieved 100% kill.

EXAMPLE 4

*Tetranychus telarius*; Experiment A

Potted bush beans exhibiting the second pair of true leaves are sprayed to runoff in a spray cabinet with aqueous formulations of the active ingredients. The plants, exhibiting heavy mite attack and numerous eggs, are placed on a rotating table and are sprayed from all sides with a total of 50 ml of spray liquor.

The action is assessed after 5 days by means of a binocular microscope, attention being paid to the fact that all stages are covered. During this period, the plants are kept under normal greenhouse conditions.

In this experiment, a concentration of 10 ppm of compound no. 13 achieved 80% kill.

EXAMPLE 5

*Tetranychus telarius*; Experiment B

Potted bush beans exhibiting the second pair of true leaves are sprayed to runoff in a spray cabinet with aqueous formulations of the active ingredients. The plants are placed on a rotating table and are sprayed from all sides for approx. 20 seconds with a total of 50 ml of spray liquor. After 24 hours, leaf pieces under heavy mite attack are placed on the plants. The action is assessed after 12 days.

In this experiment, a concentration of 40 ppm of compound no. 13 achieved 100% kill.

We claim:

1. A pyrimidine of the formula Ia
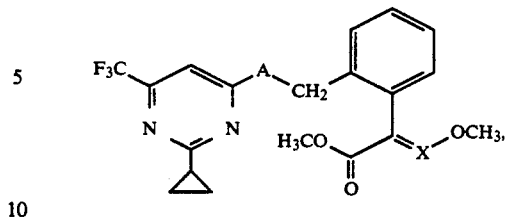
where A is oxygen or sulfur and X is CH or N.
2. A pesticidal composition containing an effective amount of a pyrimidine of the formula Ia as set forth in claim 1 and inert additives.
* * * * *